United States Patent [19]

Rhodes et al.

[11] Patent Number: 5,861,139

[45] Date of Patent: *Jan. 19, 1999

[54] DIRECT LABELING OF PEPTIDES WITH METAL IONS

[76] Inventors: Buck A. Rhodes, 1104 Stanford Dr., NE.; Paul O. Zamora, 1514 Vassar, NE., both of Albuquerque, N. Mex. 87106

[*] Notice: The term of this patent shall not extend beyond the expiration date of Pat. Nos. Re. 35,457, Re. 35,500, 5,028,985 and 5,102,990.

[21] Appl. No.: 464,529

[22] Filed: Jun. 5, 1995

Related U.S. Application Data

[63] Continuation of Ser. No. 816,477, Jan. 3, 1992, Pat. No. 5,460,785, which is a continuation-in-part of Ser. No. 391,474, Aug. 9, 1989, Pat. No. 5,078,985.

[51] Int. Cl.⁶ .......................... A61K 51/00; A61M 36/14
[52] U.S. Cl. ...................... 424/1.69; 424/9.34; 424/149
[58] Field of Search ............................... 424/1.49, 1.69, 424/9.34

[56] References Cited

U.S. PATENT DOCUMENTS

| | | | |
|---|---|---|---|
| Re. 35,457 | 2/1997 | Rhodes | 424/1.49 |
| Re. 35,500 | 5/1997 | Rhodes | 424/1.49 |
| 3,812,264 | 5/1974 | Nouel | 424/1 |
| 4,424,200 | 1/1984 | Crockford et al. | 424/1.1 |
| 4,472,371 | 9/1984 | Burchiel et al. | 424/1.1 |
| 4,478,815 | 10/1984 | Burchiel et al. | 424/1.1 |
| 4,485,101 | 11/1984 | Coy et al. | 424/177 |
| 4,853,371 | 8/1989 | Coy et al. | 514/12 |
| 4,871,717 | 10/1989 | Coy et al. | 514/11 |
| 4,877,868 | 10/1989 | Reno et al. | 530/390 |
| 4,904,642 | 2/1990 | Coy et al. | 514/806 |
| 4,988,496 | 1/1991 | Srinivasan et al. | 424/1.11 |
| 5,011,676 | 4/1991 | Thakur | 424/1.1 |
| 5,053,493 | 10/1991 | Pak et al. | 530/402 |
| 5,061,641 | 10/1991 | Schochat et al. | 436/545 |
| 5,078,985 | 1/1992 | Rhodes | 424/1.1 |
| 5,102,990 | 4/1992 | Rhodes | 530/391.5 |
| 5,116,596 | 5/1992 | Bremer et al. | 424/1.1 |
| 5,128,119 | 7/1992 | Griffiths | 424/1.1 |
| 5,225,180 | 7/1993 | Dean et al. | 424/1.1 |
| 5,277,892 | 1/1994 | Rhodes | 424/1.69 |
| 5,317,091 | 5/1994 | Subramanian | 424/1.53 |
| 5,328,679 | 7/1994 | Hansen et al. | 424/1.49 |
| 5,334,708 | 8/1994 | Chang et al. | 530/391.5 |
| 5,346,687 | 9/1994 | Rhodes | 424/1.49 |
| 5,443,815 | 8/1995 | Dean et al. | 424/1.41 |
| 5,443,816 | 8/1995 | Zamora et al. | 424/1.69 |
| 5,460,785 | 10/1995 | Rhodes et al. | 424/1.49 |
| 5,514,363 | 5/1996 | Shochet et al. | 424/1.49 |

FOREIGN PATENT DOCUMENTS

| | | |
|---|---|---|
| 0 271 806 | 6/1988 | European Pat. Off. . |
| 0 389 180 | 9/1990 | European Pat. Off. . |
| 0 419 203 | 3/1991 | European Pat. Off. . |
| 2043459 | 5/1969 | France ............. A61K 27/00 |
| 2225579 | 6/1990 | United Kingdom . |
| 04164 | 7/1987 | WIPO ............. A61K 49/02 |
| 88/07382 | 10/1988 | WIPO . |
| WO 89/04666 | 6/1989 | WIPO . |
| 15626 | 12/1990 | WIPO . |
| GB90/00933 | 12/1990 | WIPO ............. C07K 5/08 |
| WO 90/15626 | 12/1990 | WIPO . |
| WO 91/01144 | 2/1991 | WIPO . |
| 02547 | 3/1991 | WIPO ............. A61K 49/02 |
| US92/00757 | 8/1992 | WIPO ............. A61K 49/02 |

OTHER PUBLICATIONS

Albert, R., et al., A ISomatostatin Analogue to Image SS–Receptor–Positive Tumours,*12th American Peptide Symposium,* Abstract LM10 (1991).

Bakker, W.H., et al., "In Vivo Use of a Radiodinated Somatostatin Analog: Dynamics, Metabolism, and Binding to Somatostatin Receptor–Positive Tumors in Man," *J. Nucl. Med.,* vol. 32, No. 6 (1991).

Bakker, W.H., et al., "Receptor Scintigraphy with a radio-iodinated Somatostatin Analog: Radiolabeling, Purification, Biologic Activity, and In Vivo Application in Animals," *J. Nucl. Med.,* vol. 31, No. 9, (Sep. 1990).

Kwekkeboom, D.J., "[$^{In-111-DTPA-D-Phe}$]$_1$–Octreotide Scintigraphy in Neuro–Endocrine Tumors," *The Journal of Nuclear Medicine, Proc. of 38th Ann. Meeting,* vol. 32, No. 5, p. 981, (1991).

"The Labeling of High Affinity Sites of Antibodies with 99mTc," by Chang H. Paik et al., Int. J. Nucl. Med. Biol., vol. 12, No. 1, pp. 3–8 (1985).

Anderson, P., et al., "Antibodies Labeled with $^{199}$Au: Potential for $^{199}$Au: for Radioimmunotherapy," Nucl. Med. Biol., vol. 15, No. 3, pp. 293–297, (1988).

Deshpande, S.V., et al., "Copper–67–Labeled Monoclonal Antibody Lym–1, A Potential Radiopharmaceutical for Cancer Therapy: Labeling and Biodistribution in RAJI Tumored Mice," J. Nucl. Med., vol. 29, No. 2, pp. 217–225, (Feb. 1988).

DeNardo, G.L., et al., "Requirements for a Treatment Planning System for Radioimmunotherapy," Int. J. Radiol. Oncology Biol. Phys., vol. 11, pp. 335–348, (1985).

Esser, Peter D., Appendix, "Radioactive Tracers," *Freeman &Johnsons Clinical Radionuclide Imaging,* 3rd Ed., pp. 1491–1513 (1984).

Granowska, M., et al., "A Tc–99m Labelled Monoclonal Antibody, PR1A3, for Radioimmunoscintigraphy, RIS, of Colorectal Cancer," Proceedings of the 36th Annual Meeting, J. Nucl. Med., vol. 30, p. 748 (No. 80), (1989).

(List continued on next page.)

*Primary Examiner*—Gary E. Hollinden
*Assistant Examiner*—Dameron Jones
*Attorney, Agent, or Firm*—Darby & Darby

[57] ABSTRACT

Proteins containing one or more disulfide bonds or monosulfides are labeled with medically useful metal ions for use in diagnosis and treatment of a variety of pathologic conditions. Labeling is accomplished with a variety of metals, including radiometals, by using a reducing agent to reduce the disulfide bonds to thiolate groups; excess reducing agent, reaction by-products and any impurities are removed; and, a source of Sn (II) agent is added to the thiolate-containing protein. The resulting product may be stored frozen or lyophilized, with labeling accomplished by the addition of the medically useful metal ions.

18 Claims, No Drawings

OTHER PUBLICATIONS

Green, M.A., et al., Review, "Gallium Radiopharmaceutical Chemistry," Nucl. Med. Biol., vol. 16, No. 5, pp. 435–448, (1989).

Hainfeld, James F., et al., "Radioactive Gold Cluster Immunoconjugates: Potential Agents for Cancer Therapy," Nucl. Med. Biol., vol. 17, No. 3, pp. 287–294, (1990).

Mercer–Smith, Janet A., et al., "The Biodistribution of Radiocopper–Labeled Compounds," *Copper Bioavailability and Metabolism,* C. Kies, Ed., pp. 103–121, (1990).

Pak, K.Y., et al., "A Rapid and Efficient Method for Labeling IgG Antibodies with Tc–99m and Comparison to Tc–99m FAB' Antibody Fragments," Scientific Papers, Proceedings of the 36th Annual Meeting, J. Nucl. Med., vol. 30, No. 5, p. 793 (No. 268), (1989).

Pietersz, G.A., et al., Special Invited Article, "The Use of Monoclonal Antibody Conjugates for the Diagnosis and Treatment of Cancer," Immunology and Cell Biology, vol. 65, Pt. 2, pp. 111–125, (1987).

Rayudu, G.V.S., "Production of Radionuclides for Medicine," Sem. Nucl. Med., vol. 44, pp. 100–110, (1990).

Rhodes, Buck A., et al., "Technetium–99m Labeling of Murine Monoclonal Antibody Fragments," J. Nucl. Med., vol. 27, No. 6, pp. 685–693, (May 1986).

Roberts, Jeanette C., et al., "Preparation and Characterization of Copper–67 Porphyrin–Antibody Conjugates," J. Immunol. Meth., vol. 105, pp. 153–164, (1987).

Roberts, Jeanette C., et al., "Labeling Antibodies with Copper Radionuclides Using N–4–Nitrobenzyl–5–(4–carboxyphynyl)–10,15, 20–tris(4–sulfophenyl) Porphine," Appl. Radiat. Isot., vol. 40, No. 9, pp. 775–781, (1989).

Som, P., et al., "Radioimmunoimaging of Experimental Thrombi in Dogs Using Technetium–99–m–Labeled Monoclonal Antibody Fragments Reactive with Human Platelets," J. Nucl. Med., vol. 27, No. 8, pp. 1315–1320, (Aug. 1986).

Schwarz, A., et al., "A Novel Approach to Tc–99m–Labeled Monoclonal Antibodies," Poster Sessions, Proceedings of the 34th Ann. Mtg., J. Nucl. Med., vol. 28, No. 4, p. 721 (No. 695), (Apr. 1987).

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:1:

Cys Asp Pro Gly Tyr Ile Gly Ser Arg
1               5

DIRECT LABELING OF PEPTIDES WITH METAL IONS

CROSS-REFERENCE TO RELATED APPLICATIONS

This is a continuation of application Ser. No. 07/816,477, filed on Jan. 3, 1992, now U.S. Pat. No. 5,460,785, issued Oct. 24, 1995, which is a continuation-in-part application of U.S. patent application Ser. No. 07/391,474, filed Aug. 9, 1989, now U.S. Pat. No. 5,078,985, issued Jan. 7, 1992 entitled *Radiolabellng Antibodies and Other Proteins with Technetium or Rhenium by Regulated Reduction*, and is related to U.S. patent application Ser. No. 07/565,275, filed Aug. 8, 1990, now U.S. Pat. No. 5,102,990, entitled *Direct Radiolabellng of Antibodies and Other Proteins with Technetium or Rhenium*, a divisional application filed Dec. 27, 1991, entitled *Composition for Radiolabeling Antibodies and Other Proteins by Regulated Reduction*, Ser. No. 07/815,122, now abandoned and a continuation application filed Dec. 27, 1991, Ser. No. 07/815,123, now abandoned entitled *Method for Radiolabellng Antibodies and Other Proteins by Regulated Reduction*, the teachings of all of which are incorporated herein by reference. A related application entitled *Direct Radiolabeling of Antibody Against Stage Specific Embryonic Antigen for Diagnostic Imaging* now U.S. Pat. No. 5,346,687 was filed with Ser. No. 07/816,477, and the specification thereof is incorporated herein by reference.

LICENSE RIGHTS

The U.S. Government has a paid-up license in this invention and the right in limited circumstances to require the patent owner to license others on reasonable terms as provided for by the terms of Small Business Innovative Research Grant No. CA50799 awarded by the National Cancer Institute, Department of Health and Human Services.

BACKGROUND OF THE INVENTION

1. Field of the Invention (Technical Field):

This invention relates to a method and composition for labeling proteins, peptides and amino acids, including antibodies, with a variety of metals ions, including radioisotopes of a variety of radiometals.

2. Background Art:

The use of radioisotopes to label proteins is well known. These compositions can be used in in vitro assays; can be administered to the human body to visualize or monitor functioning of various parts of the body or to determine the presence and location of particular antigens, antibodies, hormones or the like; and can be used in the treatment of various disease states. A variety of radioisotopes, including isotopes of technetium, indium, copper, rhenium, gold and arsenic have been used to label proteins.

Antibodies and antibody fragments have been labeled with a number of radionuclides for use in clinical diagnosis. These radionuclides include $^{131}$I, $^{125}$I, $^{123}$I, $^{99m}$Tc, $^{67}$Ga, and $^{111}$In. So far, only $^{99m}$Tc and $^{111}$In-labeled antibody preparations are widely used in clinical settings. For diagnostic imaging, both isotopes should be ideal; however, clinical limitations, including affinities for liver and kidneys that limit detection of abdominal diseases, have prompted searches for other imaging radionuclides.

Antibodies have also been labeled with a variety of radionuclides for potential use in targeted immunotherapy (Pietersz G A, Kannellos J, Smyth M J, et al. The use of monoclonal antibody conjugates for the diagnosis and treatment of cancer. *Immunol Cell Biol* 65:111–125, 1987). These radionuclides include $^{90}$Y, $^{188}$Re, and $^{186}$Re, and to a lesser extent $^{199}$Au and $^{67}$Cu. $^{131}$I has also been used. With the exception of $^{131}$I, all the methods currently used to conjugate these radiometals to antibodies involve the use of chelating groups chemically attached to the antibody. $^{67}$Cu is one radionuclide that has been specifically recommended for use as a therapeutic radionuclide when bound to antibodies (DeNardo G L, Raventos A, Hines H H, et al. Requirements for a treatment planning system for radioimmunotherapy. *Int J Radiol Oncology Biol Phys* 11:335–348, 1985). $^{199}$Au-conjugated monoclonal antibodies have also been suggested for potential use as cancer therapeutic agents.

$^{67}$Cu has been attached to monoclonal antibodies through chelates, e.g., a macrocycle chelate (6-para-nitrobenzyl-1,4,8,11-tetraazacyclotetradecane-N,N',N'',N''') (Deshpande S V, DeNardo S J, Meares C F, et al. Copper-67-labeled monoclonal antibody Lym-1, A potential radiopharmaceutical for cancer therapy: labeling and biodistribution in RAJI tumored mice, *J Nucl Med* 29:217–225, 1988), and porphyrins (Roberts J C, Figard S D, Mercer-Smith J A, et al. Preparation and characterization of copper-67 porphyrin-antibody conjugates. *J Immunol Meth* 105:153–164, 1987). The macrocycle chelate, but not the porphyrin conjugate, was evaluated in an animal model system. Both $^{64}$Cu and $^{67}$Cu, have been conjugated by the porphyrin method to antibodies and autoantigenic peptides (Roberts J C, Newmyer S L, Mercer-Smith J A, Schrerer and Lavallee D K. Labelling antibodies with copper radionuclides using N-4-nitrobenzyl-5-(4-carboxyphenyl)-10,15,20-tris(4-sulfophenyl) porphine. *Appl Radiat Isot* 40:775–781, 1989). Biodistribution studies of radiocopper-labeled antibodies have shown that blood clearance is rapid and uptake to the bone is low (Mercer-Smith J A, Cole D A, Roberts J C, et al. The biodistribution of radiocopper-labeled compounds. In: C Kies (ed), *Copper Bioavailability and Metabolism*, pp 103–121, 1990).

Antibodies have been labeled with $^{199}$Au, in the form of gold clusters (Hainseld J F, Foley C J, Srivastava S C, et al. Radioactive gold cluster immunoconjugates: Potential agents for cancer therapy. *Nucl Med Biol* 17:287–294, 1990), and with $^{199}$Au and $^{195}$Au, as complex ions in citrate buffered saline (Anderson P, Vaugan A T M, and Varley N R. Antibodies labeled with $^{199}$Au: Potential use of $^{199}$Au for radioimmunotherapy. *Nucl Med Biol* 15:293–297, 1988).

Antibodies and other proteins have been directly labeled. Although several direct methods have been reported, the first direct method capable of providing a sufficiently strong bond between the protein and technetium-99m for In vivo applications was the direct or pretinning method described in U.S. Pat. No. 4,424,200, entitled *Method for Radiolabeling Proteins with Technetium-99m*, to Crockford, D. R., and Rhodes, B. A. In this method, a single reduction compound, consisting of stannous [Sn(II)] chloride and other salts which serves both to reduce the protein, thereby exposing the disulfide bonds, and to reduce the sodium pertechnetate, is used. With this method, many proteins can be successfully radiolabeled with $^{99m}$Tc. Several investigators have reported on the use of this method (Rhodes, B. A., et al, "Technetium-99m labeling of murine monoclonal antibody fragments," *J Nucl Med* 27:685–693, 1986; Som, P., et al, "Radioimmunoimaging of experimental thrombi in dogs using technetium-99m-labeled monoclonal antibody fragments reactive with human platelets," *J Nucl Med* 27:1315–1320, 1987).

Equivalent methods for direct labeling have been reported (Schwarz, A., and Steinstruaber, A., "A novel approach to Tc-99m-labeled monoclonal antibodies," *J Nucl Med* 28:721, 1987; Pak, K. Y., et al, "A rapid and efficient method for labeling IgG antibodies with Tc-99m and comparison to Tc-99m Fab'". *J Nucl Med* 30:793, 1989; Granowska, M., et al, "A Tc-99m-labeled monoclonal antibody, PR1A3, for radioimmunoscintigraphy," *J Nucl Med* 30:748, 1989). In the equivalent methods disulfide reducing agents other than stannous salts were used. Pak et al used dithiothreitol to reduce the disulfide bonds of the antibody; Swartz and Steinstrauber, and Granowska et al used 2-mercaptoethanol. Also some of these investigators (Swartz and Steinsbruaber, and Granowska et al) reduced the Tc-99m prior to adding it to the reduced antibody, which adds steps to the original procedure.

Reno, J. W., et al, U.S. Pat. No. 4,877,868, *Radionuclide Antibody Coupling*, uses dithiothreitol (DTT) to reduce the disulfide groups of the protein, then protects the reactive sulfides with Zn (II) or other sulfhydryl group derivatizing reagents. Tartrate salts are used to complex and transfer the reduced radionuclide. This method uses potentially toxic chemicals, such as dithiothreitol, to reduce the antibody. It also requires multiple steps to radiolabel the protein.

Thakur, M. L., U.S. Pat. No. 5,011,676, *Method to Directly Radiolabel Antibodies for Diagnostic Imaging and Therapy*, used sodium ascorbate to reduce the disulfide groups of antibodies. However, this method cannot be adapted to single-step, direct labeling; it is required to reduce the radionuclide prior to adding the radionuclide to the sodium ascorbate reduced protein. In a preferred embodiment of the Thakur method, a separate vial is utilized, in which sodium dithionite is used to reduce the radionuclide, producing dithionite reduced radionuclide.

There are useful metals for magnetic resonance imaging, including gadolinium, manganese, copper, iron, gold and europium, which are not radioisotopes. Examples also include ions of a lanthinide element of atomic numbers 57–70 or ions of transition metals of atomic numbers 21–29 and 42–44. Examples of metals which would be expected to be of potential utility in magnetic resonance imaging with proteins labeled by the methods described in the present invention include copper, iron and gold, as well as colloidal preparations of iron or gold.

So far, antibodies do not appear to have been labeled with positron-emitting radiometals, although other types of proteins (transferrin and human serum albumin) have been labeled with $^{68}$Ga (Green M A, and Welch M J. Gallium radiopharmaceutical chemistry. *Nucl Med Biol* 16:435–448, 1989). The short half-life associated with $^{68}$Ga, i.e., 68 minutes, suggests that it often may not be a suitable label for targeting antibodies, which tend to have prolonged biological half-lives.

SUMMARY OF THE INVENTION (Disclosure of the Invention)

In accordance with the present invention, a method is provided for labeling proteins with a variety of metals, including radiometals, in which a reducing agent is used to reduce the disulfide bonds in the protein; excess reducing agent, reaction by-products and any impurities are removed; and, if required for labeling with the particular metal, an optimum concentration of metal reducing agent and buffering agent are added.

The protein containing monosulfides or disulfide bonds is stably labeled with a medically useful metal ion by incubating the protein containing monosulfides or disulfide bonds with a first reducing agent, the period of incubation being sufficient to reduce available disulfide bonds to thiolate groups while preventing excessive fragmentation of the protein; then substantially removing the first reducing agent from the thiolate-containing protein; adding a source of Sn (II) agent to the thiolate-containing protein in a sufficient amount to form Sn (II)-containing and sulfur-containing complexes; and labeling the Sn (II)-containing and sulfur-containing complexes by adding the medically useful metal ion, whereby the medically useful metal ion displaces the Sn (II) agent and the metal ion and thiolate-containing protein form metal ion-containing and sulfur-containing complexes.

The protein can include peptides, oligopeptides, glycopeptides, glycoproteins, immunoglobulins, monoclonal antibodies, and polyclonal antibodies, as well as fragments of all of the foregoing. Representative types of peptides includes laminin, fibronectin, cytokines, lymphokines, hormones, serum albumin, fibrinogen, enzymes, hormones, somatostatin, urokinase, tissue plasminogen activator, and protease inhibitors. The peptide can be synthesized from amino acid building blocks, and contain a biological function domain and metal binding domain, with the metal binding domain including at least one cysteine amino acid. Regardless of the protein used, it can be chemically modified by the introduction of disulfide bonds.

The first reducing agent can include 2-mercaptoethanol; 1,4 dithiothreitol; 2,3 dihydroxybutane-1; 4 dithiol; 2-aminoethanethiol HCl; 2-mercaptoethylamine; thioglycolate; cyanide; cysteine; reduced glutathione; Sn (II); Cu (I); and Ti (II). It is possible to attach the first reducing agent to a solid phase.

The source of Sn (II) agent can include stannous tartrate, stannous glucoheptonate, stannous gluconate, stannous phosphonate, stannous chloride, and stannous fluoride. Following addition of the source of Sn (II) agent, a second reducing agent can optionally be added to the Sn (II)-containing and sulfur-containing complexes in a sufficient amount to reduce the oxidation state of the medically useful metal ion to a state whereby the medically useful metal ion displaces the Sn (II) agent and the metal ion and thiolate-containing protein forms metal ion-containing and sulfur-containing complexes. This second reducing agent can be any of the Sn (II) agents listed above. It is also possible to initially add sufficient Sn (II) agent to reduce the oxidation state of the medically useful metal ion as set forth above. The Sn (II) agent can be present in a solution including alkali metal tartrate having a pH of between approximately 5.0 and 6.0. A variety of dicarboxylic acids can also be added to the Sn (II) agent solution, including phthalate or tartrate.

After addition of the Sn (II) agent, the Sn (II)-containing and sulfur-containing complexes can be frozen in a vial, and maintained for an indefinite period before labeling by the addition of the medically useful metal ion to the vial. Similarly, after addition of the Sn (II) agent, the product can be lyophilized in a vial, and maintained for an indefinite period before labeling.

The medically useful metal ions includes ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. Some medically useful metal ions are radioactive, such as radionuclidic isotopes of indium, gold, silver, mercury, technetium, rhenium and copper. It is possible to have 85 percent or more of the radionuclide strongly bonded to the protein. The medically useful metal ion can also be paramagnetic.

The product resulting from the application of this method can be used for gamma scintigraphy, specific photon emission computerized tomography, magnetic resonance imaging, positron emission tomography and radiotherapy. One characteristic of products made by this method is that in many configurations no purification step is required prior to in vivo administration.

Accordingly, it is an object of the present invention to provide a method for direct labeling of proteins with a variety of medically useful metal ions.

It is a further object of the present invention to provide a method which results in increased labeling efficiencies utilizing medically useful metal ions.

It is a further object of the present invention to provide a method which allows use of different medically useful metal ions with the same protein, such that a product may be used in an imaging modality with one medically useful metal ion, and in a therapeutic modality with another medically useful metal ion, using the same basic method of labeling.

It is a further object of the present invention to provide a method to label proteins with medically useful metal ions without loss of the biological function of the protein due to the labeling process.

Another object of the present invention is to provide a method and product which permits labeling to be accomplished by the end user using a single vial, containing both thiolate-containing protein and stannous ions, which method requires only a single step to accomplish labeling, being the introduction of the medically useful metal ion.

Other objects, advantages, and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (Best Modes for Carrying Out the Invention)

The present invention provides a method for labeling proteins with a variety of metals, including radiometals, in which a reducing agent is used to reduce the disulfide bonds in the protein; excess reducing agent, reaction by-products and any impurities are removed; and, if required for labeling with the particular metal, an optimum concentration of metal reducing agent and buffering agent are added.

In Rhodes, B. A., U.S. Pat. No. 5,078,985 issued Jan. 7, 1992, entitled *Radiolabellng Antibodies and Other Proteins with Technetium or Rhenium by Regulated Reduction,* and in the continuation and divisional applications which derive therefrom, a method is taught in which proteins are radiolabeled with radionuclides, such as of technetium or rhenium, by a process in which the disulfide bonds of the protein are first partially reduced with stannous salts or other disulfide reducing agents, all substances other than the desired reduced protein removed by size exclusion chromatography or other purification means, and a specified, smaller amount of the radionuclide reducing agent, such as a stannous salt, is added to the reduced protein in a manner such that further reduction of the protein is limited.

In Rhodes, B. A., U.S. Pat. No. 5,102,990, issued Apr. 7, 1992, entitled *Direct Radiolabeling of Antibodies and Other Proteins with Technetium or Rhenium,* and in the continuation and divisional applications which derive therefrom, a method, product and kit are provided, wherein proteins containing one or more disulfide bonds are radiolabeled with radionuclides for use in diagnosis and treatment of a variety of pathologic conditions. Radiolabeling is accomplished by partial reduction of the disulfide bonds of the protein using Sn (II), or using other reducing agents followed by the addition of Sn (II), removal of excess reducing agent and reduction by-products, and addition of a specified amount of radionuclide reducing agent, such as stannous tartrate, with the addition accomplished in such a manner that further reduction of the protein is limited.

The methods and kits of both the '474 and '275 applications are useful in the present invention. The discussions therein pertaining to technetium and rhenium are also appropriate for the other radiometals and metal ionic forms described herein. Accordingly, the teachings of both of these applications are incorporated herein by reference.

Elements that have isotopes with potentially medically useful positron emissions include arsenic, bromine, carbon, cobalt, copper, fluorine, gallium, iron, manganese, nitrogen, oxygen, rubidium, selenium, scandium, yttrium and zinc. Examples of metals which are of clinical utility in positron emission tomography with proteins radiolabeled by the methods described in the present invention include positron emitting radionuclides of arsenic, cobalt, copper, selenium and iron.

A listing of radionuclides for nuclear medicine applications can be found in standard texts (Freeman and Johnson's Clinical Radionuclide Imaging, 3rd ed., L. M. Freeman, ed., pp 1491–1513) or in scientific reviews on radionuclides for medical applications (Rayudu G V S: Production of radionuclides for medicine. *Sem Nucl Med* 44:100–110, 1990). Isotopes of the elements numbered 26–30 (Fe, Co, Ni, Cu, Zn), 33–34 (As, Se), 42–50 (Mo, Tc, Ru, Rh, Pd, Ag, Cd, In, Sn), and 75–85 (Re, Os, Ir, Pt, Au, Hg, Tl, Pb, Bi, Po, At) are useful to label proteins and other thiolate-rich substances by the methods described in the present invention. In particular, isotopes of copper, arsenic, technetium, ruthenium, palladium, silver, rhenium, platinum, gold, mercury, lead and astatine are useful in diagnostic imaging and radiotherapy. The selection of the type of radionuclide, the nature of its reduction state and the formulation of carrier buffers and solutions will vary according to the specific application and chemistry of the element.

Based on test results and the known order of metal-binding affinity to thiolate-rich proteins, radioisotopes of the following metals can be bound to proteins, antibodies, peptides and other substances containing sulfides, by the methods described in the present invention, in the following anticipated decreasing order of binding affinity:

a) mercury, palladium, platinum, bismuth,
b) copper, silver, cadmium, gold, arsenic,
c) indium, antimony, lead, ruthenium,
d) zinc, osmium, nickel, and cobalt.

$^{67}$Cu is one of the more promising radiometals for radioimmunotherapy. It has a physical half-life of 61.5 hours and releases an abundant number of beta particles, as well as moderately abundant gamma emissions (93 and 184 keV). The 184 keV emission is well suited for conventional gamma scintigraphy, and allows prediction of therapeutic dosimetry based on actual localization information. Similarly, $^{64}$Cu (12.5-hour half-life) can be used in positron emission tomography (PET), because of its positron emission, and for therapy, because it also releases beta particles. $^{62}$Cu (2-hour half-life) is particularly attractive, as it can be produced essentially carrier-free from a generator system.

$^{72}$As can be produced essentially carrier free and with high specific activity in an experimental generator, e.g. ($^{72}$Se/$^{72}$As) at Los Alamos National Laboratory. The parent, $^{72}$Se, has a half-life of approximately 9 days, which is long enough to avoid problems with generator delivery. $^{72}$As is one of the few positron-emitting radionuclides available from a generator system. It produces two co-linear, 511 keV photons, as a result of the positron-electron annihilation, and its 26 hour-half life is extremely well suited for use with antibody fragments.

$^{194}$Au can be produced in an experimental generator, using $^{194}$Hg (1.9-year half-life) as the parent. $^{194}$Au has a half-life of 39.5 hours. This half-life is suitable for antibody (and antibody fragment) imaging of tumors, which frequently takes place 3–6 days after injection of the radiopharmaceutical to allow clearance of the blood pool background activity.

One distinguishing feature of the present invention involves the use of tin ions. Many of the transition metals have multiple oxidation states. Copper, for example, can occur as Cu(I) or Cu(II), and radioisotopes in both oxidation states bind to proteins as described in this invention. A protein radiolabeled with Cu(I), however, offers certain advantages. The methods described in this invention with stannous ion as a reducing agent appear to reduce Cu(II) to Cu(I) and result in binding in the preferred oxidation state. Additionally, the presence of unlabeled tin ions appears to result in binding to both high and low affinity transition metal binding sites. The addition of a radiometal with a higher binding constant than that of tin, such as copper, appears to displace the tin from the high affinity sites and thereby result in a metal-protein with considerable bond strengths. The tin ions appear to displace the hydrogen of the free sulfhydryl groups to protect these groups from oxidation to disulfides, and thus preserve the reactive site for binding by metal ions.

Many of the metals described above do not require reduction as with technetium and rhenium described in the '474 and '275 applications. For those metal ionic forms which do require reduction, the methods described in those applications are useful in the present invention.

In the preferred embodiment, a protein substrate containing monosulfides or disulfide bonds is labeled with a medically useful metal ion by the following method:
  a) incubating the protein with a reducing agent to reduce some or all of the disulfide bonds to thiolate groups, or to maintain monosulfides as thiolate groups;
  b) removing excess reducing agent from the protein substrate containing thiolate groups;
  c) adding a source of Sn (II) agent to the thiolate-containing protein preparation in an amount sufficient to form Sn (II)-containing and sulfur-containing complexes; and,
  d) adding a medically useful metal ion whereby the metal ion displaces the Sn (II) in the Sn (II)-containing and sulfur-containing complexes and the metal ion and thiolate-containing protein form metal ion-containing and sulfur-containing complexes.

The order of the steps may be altered, and the method will still produce metal ion-labeled proteins; the claims are therefore not limited to the order of steps presented. Specifically, it is possible, and in some cases advantageous, to add the Sn (II) to form Sn (II)-containing and sulfur-containing complexes prior to removing excess reducing agent from the protein substrate. In this way, oxidation of thiolate groups or reformation of disulfide bonds and other cross-linkages is immediately prevented.

Any protein, peptide, oligopeptide, glycopeptide, glycoprotein, amino acid sequence, chelating agent or other substrate which contains one or more disulfide bonds or one or more monosulfides, including fragments of any of the foregoing or molecules formed by attaching or complexing any of the foregoing to another molecule, can be labeled in accordance with this invention. Representative suitable substrates include human serum albumin, fibrinogen, urokinase, gamma globulin, laminin, fibronectin, cytokines, lymphokines, enzymes, enzyme inhibitors, hormones, glycoproteins, oligopeptides, peptides, both natural and synthetic, other proteins and immunoglobulins. The term "protein" as used throughout the specification and claims is intended to include all of the foregoing substances. The protein is typically of mammalian origin, but also includes proteins of plant origin and proteins from prokaryotic cells. Methods of attaching or complexing proteins to other molecules, such as lipids and carbohydrates, including liposomes, is known to those skilled in the art.

Immunoglobulins, a type of protein, which can be labeled, include antibodies and antibody fragments, of any species, and include both polyclonal and monoclonal antibodies made by any means, as well as chimeric and genetically engineered antibodies, hybrids, and fragments of all of the foregoing. This includes immunoglobulins of any class, such as IgG, IgM, IgA, IgD or IgE, of any species origin, including human beings, chimeric antibodies or hybrid antibodies with dual or multiple antigen or epitope specificities, and fragments of all of the foregoing, including F(ab')$_2$, F(ab)$_2$, Fab', Fab and other fragments, including hybrid fragments, and further includes any immunoglobulin or any natural, synthetic or genetically engineered protein that functionally acts like an antibody by binding to a specific antigen to form a complex, including single chain antibodies. The term "antibody" or "antibodies", and the phrase "monoclonal antibody component", as used throughout the specification and claims is intended to include all such antibodies and antibody fragments.

Components of the basement membrane, and in particular, laminin, fibronectin, and fragments of laminin and fibronectin are proteins which can be labeled in accordance with this invention. Enzymes include urokinase and tissue plasminogen activator. Hormones and hormone subunits, and in particular somatostatin, can similarly be labeled.

Proteins used in this invention can be produced in bulk by a number of methods known to those skilled in the art. Production methods include use of prokaryotic cells, eukaryotic cells, E. coli, Chinese hamster ovary cells, and hybridomas. These cells be modified by genetic engineering techniques including gene transection, hybridoma technology, recombinant DNA technology, or gene splicing to produce the protein. The protein can also be produced by chemical synthesis from amino acid building blocks using conventional techniques. The protein may also be produced by enzymatic degradation, a means used to produce a variety of antibody fragments.

It is possible to chemically modify the protein by the introduction of disulfide bonds. A protein, even though it may not natively contain monosulfides or disulfide bonds, with attached or complexed disulfide bonds can be labeled in accordance with this invention. Means to attach or complex disulfide bonds, and chelating agents and substrates containing disulfide bonds, are known to those skilled in the art. Phytohemagglutinin, and the L-4 isolectin thereof, is an example of a protein that does not natively contain disulfide bonds. Disulfide bonds may be introduced into such proteins by chemical methods involving direct conjugation. Chemical means used to introduce disulfide bonds into proteins includes use of homofunctional crosslinkers, heterofunctional crosslinkers, and monofunctional protein modification agents. Representative chemicals which can be used to introduce disulfide bonds into proteins include 4-succinimidyloxycarbonyl-α-methyl-α-(2-pyridyldithiol)-toluene; N-succinimidyl 3-(2-pyridyldithio)propionate; sulfosuccinimidyl 6-[3-(2-pyridyldithiol) propinoamido] hexonate; dithiobis(succinimidylproprionate); 3,3'-dithiobis(sulfosuccinimidylpropionate); and sulfosuccinimidyl 2-(ρ-azidosalicylamido)ethyl-1,3'-dithropropionate.

The protein of this invention is reacted with a medically useful metal ion. The medically useful metal ion may be radioactive and generate gamma rays, beta particles, or positrons which are converted into gamma rays upon collision with electrons. Alternatively, the medically useful metal ion may be paramagnetic. The medically useful metal ion may used in diagnostic imaging procedures including gamma scintigraphy, specific photon emission computerized tomography, or positron emission tomography. The medically useful metal ion may also be used in magnetic resonance imaging or radiotherapy.

The type of medically useful metal ion depends on the specific medical application. Particularly attractive metal ions can be found in the group consisting of elements 26–30 (Fe, Co, Ni, Cu, Zn), 33–34 (As, Se), 42–50 (Mo, Tc, Ru, Rh, Pd, Ag, Cd, In, Sn), and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy.

Incubation of the protein with a reducing agent causes reduction of some or all of the disulfide bonds to thiolate groups, and in the case of proteins with monosulfides, causes the monosulfides to be maintained as thiolate groups. Numerous reducing agents have been described and are known to those skilled in the art. Particularly attractive types of reducing agents include 2-mercaptoethanol; 1,4 dithiotheitol; 2,3 dihydroxylbutane-1,4-dithiol; 2-aminoethanethiol HCl; 2-mercaptoethylamine; thioglycolate; cyanide; cysteine; reduced glutathione; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the protein requires disulfide bond reduction depends on the nature of the protein and its intended medical application. In any event, reduction is halted before excessive fragmentation of the protein or loss of the biological function of the protein occurs.

In one specific embodiment, Sn (II) is used as a reducing agent at a concentration of 5 mM. In this embodiment the Sn (II) is dissolved in a buffer composed of 10 mM tartrate and 40 mM phthalate, pH 5.5, and the Sn (II) buffer admixed with a protein substrate at a concentration of 8.3 mg/ml. The reduction reaction is allowed to proceed for 21 hours at room temperature, after which time the reaction is terminated by removing excess Sn (II) ions by molecular sieve chromatography. One means of molecular sieve chromatography employs Sephadex G-25, with the chromatography gel pre-equilibrated, and the protein eluted in 0.9% NaCl or other suitable buffer.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forms of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced proteins are highly reactive and can interact to form disulfide bonds. The use of Sn (II) is believed to minimize the reformation of disulfide bonds. Sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the protein, the nature of the protein, the relative and absolute number of thiolate groups and the metal ion to be used. In one embodiment stannous tartrate is used at a concentration of 1.25 mM. The stannous tartrate is added to the protein after removal of the protein-reducing agent. The stannous tartrate is prepared in a buffer composed of 10 mM tartrate and 40 mM phthalate, pH 5.6, and is added to protein to yield a final concentration of 1 mg/ml protein solution.

Sn (II) can be stabilized by use of dicarboxylic acids, such as phthalate and tartrate. A wide range of dicarboxylic acids, known to those skilled in the art, may be similarly used to stabilize the Sn (II) and/or to act as a buffer. If the phthalate and tartrate are in molar excess relative to the Sn (II), then these dicarboxylic acids also stabilize the medically useful metal ion in a form which can react with the protein. In one embodiment tartrate and phthalate are used in the Sn (II) agent at concentrations of 10 mM and 40 mM, respectively.

Similarly, the Sn (II) and the medically useful metal ion may be stabilized by amino acids used singly or in combination with other agents. The type of amino acid used and the specific concentration depends on the nature of the protein and its intended use. In one embodiment, glycine is used at a concentration of 0.1–10 mm, and in another, histidine is used at a concentration of 0.1–10 mM. Penicillamine is an amino acid which may also be used.

The protein may be stored frozen in bulk form after disulfide bond reduction and the removal of excess reducing agent. Alternatively, the protein may be stored in bulk form or in unit dose form after addition of the Sn (II). Similarly, the protein may be stored lyophilized during or after processing. For example, in one embodiment the protein is stored in vials after introduction of the Sn (II). Methods used in lyophilization of proteins are known to those skilled in the art. Either frozen or lyophilized preparations may be maintained for an indefinite period before labeling by the addition of the medically useful metal ion.

In both the frozen and lyophilized storage forms, excipients may be added to the protein to minimize damage which can arise from ice-crystal formation or free-radical formation. The type of excipient and the concentration depends on the nature of the protein and the intended use. In one embodiment, glycine and inositol are used as excipients in lyophilized preparations.

A typical lyophilized preparation made by the embodiments set forth above would, upon rehydration, contain 10 mM tartrate, 40 mM phthalate, 22 pg of Sn (II), 500 pg of protein, 2 mg/ml of glycine, and 2 mg/ml of inositol. The amounts of protein and Sn (II) used in the kits would depend on the medical application, varying depending on biodistribution of the protein, imaging modality being used, type of metal ion and related factors. Similarly, the amount and type of buffer components (such as tartrate and phthalate) and excipients (such as glycine and inositol) depends on the specific application.

To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the redox state of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the protein, after which the radiolabeled preparation can be directly used in medical applications. In another embodiment, $^{67}$Cu is added in a solution of 10 mM tartrate and 40 mM phthalate at pH 5.6. In yet another embodiment, $^{188}$Re or $^{188}$Re is added to a solution of 10 mM tartrate and 40 mM phthalate, at pH 5.6, and containing Sn (II), and then heated to lower the oxidation state of Re. The resulting solution is then added to the lyophilized or frozen preparation.

In the embodiment in which $^{99m}$Tc is used, the Sn (II) is present in the protein-containing solution in sufficient excess to alter the oxidation state of the Tc ion such that it can bind to thiolate groups. Typically Tc (VII) is reduced to Tc (III), Tc (VI), and/or Tc (V). The preferred state of Tc to be added to protein preparations is as the pertechnetate ion, $(TcO_4)^-$. The Sn (II) then reacts with the pertechnetate ion resulting in a perchloro-technetium ion in which the Tc is in a lower oxidation state and is reactive with thiolate groups. Similar approaches may be used to lower the oxidation state of other medically useful metal ions for subsequent binding to thiolate groups. The type of the metal ion, its isotopic nature, and concentration would depend on the intended medical application.

The product resulting from the methods set forth herein can be used for both medical applications and veterinary applications. Typically, the product is used in humans, but may also be used in other mammals. The product may be used to monitor normal or abnormal metabolic events, to localize normal or abnormal tissues, to localize diseases, and to treat diseases. Additionally, the product may also be used to bind to blood constituents, including blood cells, lymphocytes, macrophages, platelets, and red blood cells for subsequent localization of diseases, infections, and abnormal tissues. The application and medical use of the product depends on the type of protein and the type of medically useful metal ion used.

The product can be used in a variety of medical procedures including gamma scintigraphy, specific photon emission computerized tomography, positron emission tomography, magnetic resonance imaging, and radiotherapy. The medical application of the product of this invention depends on the type of protein and the type of medically useful metal ion used.

The invention is further illustrated by the following non-limiting examples.

EXAMPLE I

Preparation of antibodies for labeling.

Human gamma globulin was obtained commercially (Gamimune$^R$ N, Cutter Biological, Elkhart, Ind.). The method used to prepare the antibody involved reduction by a 21-hour incubation in stannous ions (2 mM). The antibody was used at a concentration of 5 mg/ml and in a buffer composed of 10 mM tartrate and 40 mM phthalate, pH 5.5, containing 2 mM stannous tartrate. In some samples, 0.5 mM $CuCl_2$ was included in the reduction buffer. The reduction step was followed by buffer exchange by chromatography through Sephadex G-25 (0.9% NaCl was used for equilibration and elution). The antibody solution was then adjusted to 1.25 mM stannous tartrate by adding an appropriate amount of 10 mM tartrate/40 mM phthalate buffer, pH 5.5, containing 5 mM stannous tartrate. This method resulted in the preparation of vials containing antibody with stannous ion-reduced disulfide bonds (thiolate groups). The antibody solution in each vial contained: a) 0.5–1.0 mg of antibody, and b) a buffer composed of 10 mM tartrate and 40 mM phthalate, pH 5.6, containing 1.25 mM stannous tartrate and excipients. Both the tartrate and phthalate are dicarboxylic acids used, in part, as weak chelators and stabilizers for both the stannous ions and the radiometal.

Non-reduced IgG was prepared under identical conditions, except that no stannous ions were included in the antibody reduction step. In some cases, the non-reduced IgG was incubated for 15 minutes in 0.5 mM $CuCl_2$ (approximately 10,000 molar excess). Stannous tartrate (1.25 mM) was included in the final formulation.

Antibody Labeling with $^{67}$Cu.

$^{67}$Cu [37 MBq (1 mCi)] was obtained from the University of Missouri Research Reactor (St. Louis, Mo.) in 0.1M HCl. Specific activity was determined to be approximately 270 $\mu$Ci/$\mu$g as measured by directly-coupled plasma emission spectroscopy. The volume of the $^{67}$Cu solution was reduced to dryness under a stream of argon. In these experiments the relative amount of copper that was used was 2 $\mu$g of copper/mg of antibody. The dried residue was dissolved in 10 mM tartrate/40 mM phthalate buffer, pH 5.6, and the pH readjusted to 5.6 by the dropwise addition of 0.1M NaOH.

To label kits with $^{67}$Cu, lyophilized kits of human IgG were dissolved in 0.5 ml of 0.9% NaCl. To the dissolved IgG was added 1 ml of the $^{67}$Cu solution as prepared above. The mixture was allowed to incubate at room temperature for up to 60 minutes. An incubation period of 15–20 minutes provided slightly enhanced radiolabeling yields.

IgG, which had been previously reduced by exposure to stannous ions, bound $^{67}$Cu extremely well. Analysis of the recoveries from chromatography in Sephadex G-25 revealed that greater than 95% of the offered $^{67}$Cu was incorporated into the antibody, which eluted in the void volume (Table 1). The high binding efficiency was confirmed by TLC in 85% methanol where it was determined that 95% of the offered $^{67}$Cu was bound to the antibody. By contrast, $^{67}$Cu was found to bind poorly to non-reduced IgG as determined by filtration through Sephadex G-25, a result which was confirmed by TLC (Table 1). Because less than 10% of the offered radioactivity was found to be associated with the non-reduced IgG, extended analyses were not performed with the non-reduced IgG.

TABLE 1

Comparison of percent radioactivity using native (unreduced) human gamma globulin and stannous ion reduced human gamma globulin and assayed in various in vitro tests. Thin layer chromatography (TLC) was performed using 85% methanol as a developing solution. Binding to protein A was performed using affinity columns of protein A-agarose. "ND" means not determined.

| Test | Native IgG | Reduced IgG |
|---|---|---|
| TLC, Amount at Origin | ND | 95% |
| Sephadex G-25 Recovery | 2% | 95% |
| Protein A-Binding | ND | 89% |

Aliquots of the $^{67}$Cu-reduced IgG preparation (post Sephadex G-25 chromatography) were chromatographed over Protein A-agarose to estimate the amount of antibody-associated $^{67}$Cu. In three separate experiments, nearly 90% of the offered radioactivity was bound to the protein A-agarose column and was not eluted by large volumes of phosphate buffered saline, pH 7.4. Elution at pH 3.0 in 0.1 M glycine/HCl resulted in the elution of essentially all (96%) of the $^{67}$Cu from the protein A-agarose columns.

In initial displacement experiments using amino acid challenge followed by TLC analysis, $^{67}$Cu-IgG was challenged with graded concentrations of either cysteine or penicillamine. In these experiments, cysteine challenge (1, 2, 5, 10 and 20 mM), but not penicillamine challenge, resulted in a concentration dependant displacement of the bound copper. At concentrations greater than 10 mM cysteine more than 70% of the $^{67}$Cu was displaced, while penicillamine at concentrations as high as 20 mM resulted in less than 8% displacement.

EXAMPLE II

Preparation of antibodies for labeling.

Human IgG (Gamimune$^R$, Cutter Biological, Elkhart, Ind.) was used as a source of IgG and was used without additional purification. To prepare stannous-ion reduced antibody (IgG-r), the stock solution of IgG was diluted to 8.3 mg/ml in chilled, nitrogen-purged 10 mM tartrate/40 mM phthalate buffer, pH 5.6 (P/T buffer) and the resulting solution mixed (3:2) in an amber vial with P/T buffer containing 5 mM stannous tartrate. The head-space gas was purged with nitrogen, the vial sealed, and the reaction allowed to proceed for 21 hours at room temperature. At the end of the incubation period, the solution was filtered through a 0.22 micron filter and chromatographed over Sephadex G-25 pre-equilibrated in P/T buffer, thereby removing tin ions. The protein concentration was determined calorimetrically and the IgGr mixed (7:3) with P/T buffer containing 1.25 mM stannous tartrate and excipients. Aliquots of 0.5 ml were dispensed into individual vials and lyophilized. Upon rehydration with 0.5 ml of water each kit contained 0.5 mg of IgG-r, 40 mM phthalate, 10 mM tartrate, and 22 μg of stannous tartrate.

Antibody Labeling with $^{111}$Ag.

Human IgG lyophilized direct labeling kits, prepared as set forth above except that all sources of chloride ions are avoided, are radiolabeled by the addition of 10 mCi of $^{111}$Ag.

EXAMPLE III

An anti-CEA antibody was reduced using dithiothreitol. The reduced antibody was then separated into several aliquots, and different aliquots had $Hg^{+2}$, $Zn^{+2}$, $Sn^{+2}$ or $Cu^{+2}$ added. The addition of the metal ions caused precipitation of the dithiothreitol, which was removed by centrifugation. The supernatant, which contained the reduced antibody and residual metal ion, was passed through a desalting column. A solution containing nitrogen purged, 40 mM sodium phthalate, 10 mM sodium tartrate, and 1.25 mM stannous tartrate was added to give 22 μgm of stannous ion per 0.5 mg of protein. 0.5 mCi of sodium pertechnetate solution was then added to each of the different metal-treated protein preparations and binding of the radiolabeled antibody preparation to solid phase antigen (RhoChek™, RhoMed, Albuquerque, N.M.) was measured. The antibody preparation made with $Sn^{+2}$ and Zn+2 yielded over 60% specific $^{99m}$Tc binding, which is the equivalent of the result obtained with antibodies directly labeled with $^{99m}$Tc by the stannous reduction method disclosed in U.S. Pat. No. 5,102,990, issued Apr. 7, 1992 filed Aug. 9, 1990, entitled *Direct Radiolabeling of Antibodies and Other Proteins with Technetium or Rhenium;* however, the antibody preparations made with $Cu^{+2}$ or $Hg^{+2}$ yielded only about 10% specific $^{99m}$Tc binding, indicating that these metal ions bind to the same binding sites as does $^{99m}$Tc, and providing evidence that metals which form strong bonds with thiolate groups, such as radioisotopes of Cu and Hg, can be used to directly label reduced proteins.

EXAMPLE IV

Direct labeling kits were made by the methods described in Example II. $^{67}$Cu was found to be effectively bound to intact antibodies (polyclonal human IgG), as well as to antibody fragments (monoclonal anti-CEA). In these studies, greater than 98% of the $^{67}$Cu was bound to the antibody, as determined by thin layer chromatography. With the polyclonal human IgG preparation, approximately 80% of the labeled material bound to protein A; with the monoclonal antibody fragment preparation, approximately 30% of the material was immunoreactive.

EXAMPLE V

Labeling of Human IgG with $^{111}$In Chloride.

Human IgG direct labeling kits were made by the methods described in Example II. $^{111}$In chloride in 0.1M HCl was obtained commercially. The $^{111}$In containing solution was added to 10 mM tartrate/40 mM phthalate buffer, pH 5.6, and the pH readjusted to 5.6 by the dropwise addition of 0.1M NaOH. Radiolabeling was performed by reconstituting the freeze-dried kits with 0.9% saline (U.S.P.), then adding the buffered and pH-adjusted $^{111}$In. The labeling reaction was allowed to proceed for 30 minutes. At the end of the 30-minute reaction period, the mixture containing the radiolabeled antibody was analyzed by high pressure liquid chromatography. By monitoring the radioactivity and the absorbance at 280 nm, it was determined that $^{111}$In co-eluted with the IgG, indicating that binding had occurred. Analysis of the overall profile indicated that 59% of the analyzed radioactivity was associated with the antibody. Thin layer chromatography on siliconized paper, using 85% aqueous methanol as a solvent, revealed that less than 3% $^{111}$In was free.

EXAMPLE VI

Labeling of Human IgG with Chelated $^{111}$In.

Human IgG direct labeling kits were made by the methods described in Example II. Chelated $^{111}$In was purchased commercially as $^{111}$In-oxine. The $^{111}$In-containing solution was added to 10 mM tartrate/40 mM phthalate buffer, pH 5.6. The lyophilized kits were radiolabeled by reconstituting the kits with 0.9% saline (U.S.P.), then adding the buffered, chelated $^{111}$In. The labeling reaction was allowed to proceed for 60 minutes.

At the end of the 60-minute reaction period, the mixture containing the radiolabeled antibody was analyzed by high pressure liquid chromatography. By monitoring the radioactivity and the absorbance at 280 nm, it was determined that $^{111}$In co-eluted with the IgG, indicating that transchelation had occurred. Analysis of the overall profile indicated that 65% of the analyzed radioactivity was associated with the antibody. Thin layer chromatography on siliconized paper, using 85% aqueous methanol as a solvent, revealed that approximately 3% of the $^{111}$In was free.

EXAMPLE VII

Labeling of Human IgG with $^{72}$As.

Human IgG direct labeling kits are made by the methods described in Example II. $^{72}$As is a positron emitter which can be produced from a generator system. $^{72}$As is normally supplied in 0.1M HCl. The $^{72}$As-containing solution is added to 10 mM tartrate/40 mM phthalate buffer, pH 5.6, and the pH readjusted to pH 5.6 by the addition of 0.1M NaOH. The lyophilized kits are radiolabeled by reconstitution with 0.9% saline (U.S.P.), then adding the buffered, pH-adjusted $^{72}$As. The reaction is allowed to proceed for up to thirty minutes. At the end of the incubation period, the $^{72}$As is bound to the IgG. Any residual unbound radionuclide is separated from the radiolabeled antibody by molecular sieve chromatography, ion exchange chromatography, affinity chromatography or other means known in the art.

EXAMPLE VIII

Labeling of Laminin with $^{99m}$Tc.

Laminin nonapeptide has application as a tracer molecule for a variety of disease states, including tracking and locating cancer cells with a high metastatic potential and localization of blood clots. The laminin nonapeptide has a sequence of Cys-Asp-Pro-Gly-Tyr-Ile-Gly-Ser-Arg (SEQ. ID NO.1), with the thiolate of cysteine presumptively used to bind $^{99m}$Tc. The laminin nonapeptide, supplied as a lyophilized material (Bachem), was dissolved directly in nitrogen-purged 10 mNM/40 mM tartrate/phthalate buffer, pH 5.5. The dissolved laminin nonapeptide was adjusted to 1 mg/ml in 10 mM tartrate/phthalate buffer containing 40 μg/ml of stannous tartrate, and labeled by the addition of sodium pertechnetate. The labeling reaction was allowed to proceed for 30 minutes. Quantitative radio-HPLC showed that virtually all $^{99m}$Tc (97% average in 4 experiments) was associated with the laminin nonapeptide.

Studies were also conducted comparing the binding of $^{99m}$Tc-laminin nonapeptide and $^{99m}$Tc-human polyclonal IgG to LS-174T colon carcinoma cells. The $^{99m}$Tc-human polyclonal IgG served as a negative control in these experiments. LS-174T is a cell line derived from a primary Duke's B tumor. In this study, LS-174T cells were grown in cell culture, and the cells removed by treatment with 3 mM EDTA in PBS, pH 7.4. The cells in EDTA were added to complete medium, diluted as required, and 5 ml of suspended cells used in experiments. Aliquots of $^{99m}$Tc-laminin nonapeptide and $^{99m}$Tc-human IgG containing approximately equal radioactivity were added to samples, mixed and allowed to incubate 30 minutes. Cells were collected by centrifugation, washed twice, and the final radioactivity counted. All experiments were done in triplicate.

TABLE 2

Comparison of binding of $^{99m}$Tc-laminin nonapeptide and $^{99m}$Tc-human IgG to LS-174T colon carcinoma cells.

| Sample | Final Binding (CPM) | Percent of Control |
| --- | --- | --- |
| EXPERIMENT ONE (n = 3) | | |
| $^{99m}$Tc-Human IgG (control) | 40,568 ± 11,275 | 100% |
| $^{99m}$Tc-Laminin | 98,194 ± 30,422 | 242% |
| EXPERIMENT TWO (n = 3) | | |
| $^{99m}$Tc-Human IgG (control) | 91,198 ± 41,545 | 100% |
| $^{99m}$Tc-Laminin | 276,977 ± 21,828 | 304% |

The preceding examples can be repeated with similar success by substituting the generically or specifically described reactants and/or operating conditions of this invention for those used in the preceding examples.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

What is claimed is:

1. A method of labeling a peptide containing at least one disulfide bond with a medically useful metal ion to obtain stable labeling, comprising the steps of:

a) incubating the peptide containing at least one disulfide bond with a first reducing agent, the period of Incubation being sufficient to reduce said at least one bond to a thiolate group while preventing excessive fragmentation of the peptide;

b) adding a source of a first Sn(II) agent to the reduced peptide to allow formation of Sn(II)-containing and sulfur-containing complexes;

c) purifying the reduced peptide with Sn(II)-containing and sulfur-containing complexes to substantially remove the first reducing agent and impurities; and d) radiolabeling the purified reduced peptide with Sn(II)-containing and sulfur-containing complexes by adding the radionuclide, whereby the complexed Sn(II) agent reduces the radionuclide, and the reduced radionuclide and reduced peptide form radionuclide-containing and sulfur-containing complexes.

2. A method of radiolabeling a peptide comprising at least one sulfur atom with a radionuclide to obtain stable labeling of said peptide, comprising the steps of:

a) incubating the peptide with Sn (II), the period of incubation being sufficient to reduce a portion of any disulfide bonds and to form a first complex comprising Sn (II)-containing and sulfur-containing complexes, while preventing excessive fragmentation of the peptide;

b) thereafter complexing free Sn agents with a subsequently added polyaminocarboxylic acid complexing agent so as not to further reduce the peptide, while retaining complexed Sn agents for reducing radionuclide, the radionuclide to be added in a subsequent step; and c) radiolabeling the Sn(II)-containing and sulfur-containing complexes by adding the radionuclide whereby the complexed Sn(II) agents reduce the radionuclide and the reduced radionuclide forms the radionuclide-containing and sulfur-containing complex.

3. The method of claim 2 wherein the amino acid is cysteine.

4. The method of claim 2 wherein the Sn (II) is a member selected from the group consisting of stannous tartrate, stannous glucoheptonate, stannous gluconate, stannous phosphonate, stannous chloride and stannous fluoride.

5. The method of claim 2 wherein following step a) and prior to step b), a reducing agent is added to the Sn (II)-containing and sulfur-containing complexes in a sufficient amount to reduce the medically useful metal ion, thereby displacing the Sn (II).

6. The method of claim 5 wherein the reducing agent is a member selected from the group consisting of stannous tartrate, stannous glucoheptonate, stannous gluconate, stannous phosphonate, stannous chloride and stannous fluoride.

7. The method of claim 2 wherein the Sn (II) in step a) is provided in a sufficient amount to reduce the medically useful metal ion thereby causing the medically useful metal ion to displace the Sn (II).

8. The method of claim 2 wherein the first complex is lyophilized prior to step b), and the lyophilized complex is stored for a substantial period of time prior to conducting step b).

9. The method of claim 2 wherein the medically useful metal ion is selected from the group consisting of ionic forms of the elements iron, cobalt, nickel, copper, zinc, arsenic, selenium, technetium, ruthenium, palladium, silver, cadmium, indium, antimony, iodine, rhenium, osmium, iridium, platinum, gold, mercury, thallium, lead, bismuth, polonium and astatine.

10. The method of claim 9 wherein the medically useful metal ion is a radionuclide selected from the group consisting of isotopes of indium, gold, silver, mercury, technetium, rhenium and copper.

11. The method of claim 10 wherein the medically useful metal ion is a radionuclide selected from the group consisting of technetium-99m, rhenium-186 and rhenium-188.

12. The method of claim 2 wherein the medically useful metal ion is radioactive.

13. The method of claim 2 wherein the medically useful metal ion is paramagnetic.

14. The method of claim 2 wherein the Sn (II) is present in a solution comprising alkali metal tartrate having a pH of between approximately 5.0 and 6.0.

15. The method of claim 2 wherein the Sn(II) is present in a solution comprising a dicarboxylic acid.

16. The method of claim 15 wherein the dicarboxylic acid is selected from the group consisting of phthalic and tartaric acid.

17. The method of claim 2 wherein the peptide is selected from the group consisting of laminin, fibronectin, cytokines, lymphokines, peptide hormones, serum albumin, fibrinogen, enzymes, urokinase, tissue plasminogen activator and protease inhibitors.

18. The product made by the process of claim 2.

* * * * *